(12) United States Patent
Luthardt et al.

(10) Patent No.: US 9,375,193 B2
(45) Date of Patent: Jun. 28, 2016

(54) APPARATUS FOR WIRELESS DATA AND POWER TRANSMISSION IN A COMPUTED TOMOGRAPHY SYSTEM

(71) Applicants: Thomas Luthardt, Bamberg (DE); Helmut Repp, Erlangen (DE)

(72) Inventors: Thomas Luthardt, Bamberg (DE); Helmut Repp, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 117 days.

(21) Appl. No.: 14/249,885

(22) Filed: Apr. 10, 2014

(65) Prior Publication Data

US 2014/0307856 A1    Oct. 16, 2014

(30) Foreign Application Priority Data

Apr. 16, 2013    (DE) .......................... 10 2013 206 826

(51) Int. Cl.
*A61B 6/00* (2006.01)
*H05G 1/08* (2006.01)
*H02J 5/00* (2016.01)
*A61B 6/03* (2006.01)

(52) U.S. Cl.
CPC . *A61B 6/56* (2013.01); *H02J 5/005* (2013.01); *H05G 1/08* (2013.01); *A61B 6/032* (2013.01)

(58) Field of Classification Search
CPC .......... A61B 6/032; A61B 6/035; A61B 6/56; A61B 6/563

USPC ........................................................ 378/4, 15
See application file for complete search history.

(56) References Cited

U.S. PATENT DOCUMENTS

| 5,140,696 | A | 8/1992 | Fox |
| 2008/0272296 | A1 | 11/2008 | Frach et al. |
| 2009/0185658 | A1 | 7/2009 | Katcha et al. |
| 2012/0082288 | A1 | 4/2012 | Friesner et al. |

FOREIGN PATENT DOCUMENTS

| DE | 19932504 | 2/2001 |
| DE | WO0188931 A1 | 11/2001 |
| DE | 102009003346 A1 | 7/2009 |
| DE | 102010041836 | 4/2012 |
| WO | WO2012041554 A1 | 4/2012 |

OTHER PUBLICATIONS

German Office Action dated Dec. 9, 2013 in corresponding German Patent Application No. DE 10 2013 206 826.6 with English translation.
Lohr, Jöstingmeier & Partners, Opposition to DE 10 2013 206 826.3, Jan. 2015, pp. 1-62.

*Primary Examiner* — Jurie Yun
(74) *Attorney, Agent, or Firm* — Lempia Summerfield Katz LLC

(57) ABSTRACT

An apparatus is configured for wireless transmission of data and electrical power between a fixed gantry part and a rotatable gantry part. The rotatable gantry part is configured to rotate about an axis of rotation of a computed tomography system. The apparatus includes a first support ring arranged on the rotatable gantry part, and a second support ring arranged on the fixed gantry part. The first support ring and the second support ring are rotationally symmetrical and L-shaped in cross-section.

20 Claims, 3 Drawing Sheets

APPARATUS FOR WIRELESS DATA AND POWER TRANSMISSION IN A COMPUTED TOMOGRAPHY SYSTEM

RELATED APPLICATIONS

This application claims the benefit of German Patent Application No. DE 102013206826.3, filed Apr. 16, 2013. The entire contents of this priority document are hereby incorporated herein by reference.

TECHNICAL FIELD

The present teachings relate generally to wireless (e.g., contactless) transmission of data and power between a fixed gantry part and a rotatable gantry part in a computed tomography system.

BACKGROUND

In conventional computer tomographs, a so-called slip ring system may be used for data transmission as described, for example, in U.S. Pat. No. 5,140,696 A. The data transmission system includes a transmission unit on the rotating part and a reception unit on the stationary part. The transmission unit has at least one radiofrequency line connected to a transmitter as a transmission antenna. The radiofrequency line is arranged at the circumference of the rotating part of the rotary frame. The reception unit includes a receiver and at least one reception antenna connected to the receiver. The reception antenna is formed by a short section of a radiofrequency line. During operation of the computer tomograph, the transmission antenna moves over a short distance past the reception antenna fastened to the stationary part. The signals propagating on the transmitting radiofrequency line cross over in the near field to the reception antenna.

In addition to data, power for the supply of electricity (e.g., to X-ray tubes) may be transmitted from the stationary part to the rotating part.

The laid-open specification DE 10 2010 041 836 A1 describes an apparatus for wireless transmission of a first electrical signal, a second electrical signal, and electrical power between a fixed gantry part and a rotatable gantry part. The rotatable gantry part may rotate about an axis of rotation of a computed tomography system. The apparatus includes a first support ring with a circular ring formation arranged on the rotatable gantry part, one or more first conductor elements arranged in or on the first support ring for drawing an electrical power, and one or more second conductor elements arranged in or on the first support ring for outputting the first electrical signals. By integrating data transmission and power transmission, costs and installation space may be reduced.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a space-saving arrangement for wireless transmission of data and power is provided.

Support rings configured for accommodating conductor tracks with a circular ring formation may be provided on a fixed gantry part and a rotatable gantry part. The support rings may be provided with an L-shaped formation and configured to have point symmetry with respect to one another.

An apparatus for wireless (e.g., contactless) transmission of data and electrical power between a fixed gantry part and a rotatable gantry part includes a first support ring arranged on the rotatable gantry part, and a second support ring arranged on the fixed gantry part. The rotatable gantry part may rotate about an axis of rotation of a computed tomography system. The first support ring and the second support ring are rotationally symmetrical and L-shaped in cross-section. As used herein, the phrase "L-shaped" means that the cross-section (e.g., as taken through the axis of rotation) has the shape of the letter "L." The first support ring has a short first limb and a long first limb. The second support ring has a short second limb and a long second limb. The first support ring and the second support ring are configured to move relative to one another, such that the short first limb and the short second limb point away from one another and are not opposite one another.

In accordance with the present teachings, the outer diameter of the support rings may be substantially smaller compared to conventional designs, thereby providing a cost savings. In addition, the computed tomography system may use less installation space and less installation time.

In some embodiments, the first support ring and the second support ring may be configured to have point symmetry with respect to one another. For example, the point of symmetry may be between the first support ring and the second support ring, thereby optimizing the position of the support rings with respect to one another.

In some embodiments, one or more first conductor elements may be arranged in or on the outer side of the long first limb. The one or more first conductor elements are configured to receive electrical power. In addition, one or more second conductor elements may be arranged in or on the outer side of the short first limb. The one or more second conductor elements are configured to transmit first electrical data signals.

In some embodiments, one or more third conductor elements may be arranged in or on the outer side of the long second limb. The one or more third conductor elements are configured to output the electrical power. In some embodiments, one or more fourth conductor elements may be arranged in or on the outer side of the short second limb. The one or more fourth conductor elements are configured to output second electrical data signals.

In some embodiments, one or more fifth conductor elements may be arranged on the second support ring. The one or more fifth conductor elements are configured to receive the first electrical data signals.

In some embodiments, one or more sixth conductor elements may be arranged in or on the first support ring. The one or more sixth conductor elements are configured to receive the second electrical data signals.

In some embodiments, each of the first conductor element and the second conductor element may have a circular ring formation.

In some embodiments, each of the third conductor element and the fourth conductor element may have a circular ring formation.

A first transmission module may be arranged on the first support ring. The first transmission module is configured to feed the first electrical data signals into the second conductor element.

In some embodiments, a first reception module may be arranged on the second support ring. The first reception module couples the first electrical data signals out of the fifth conductor element.

In some embodiments, a second transmission module may be arranged on the second support ring. The second transmission module feeds the second electrical data signals into the fourth conductor element.

In some embodiments, a second reception module may be arranged on the first support ring. The second reception module couples the second electrical data signals out of the sixth conductor element.

A plurality of transmission and reception modules may be provided. Each module may feed into or couple out of a dedicated conductor element.

A computed tomography system that includes an apparatus as described above is also provided.

DETAILED DESCRIPTION

Figure 1:
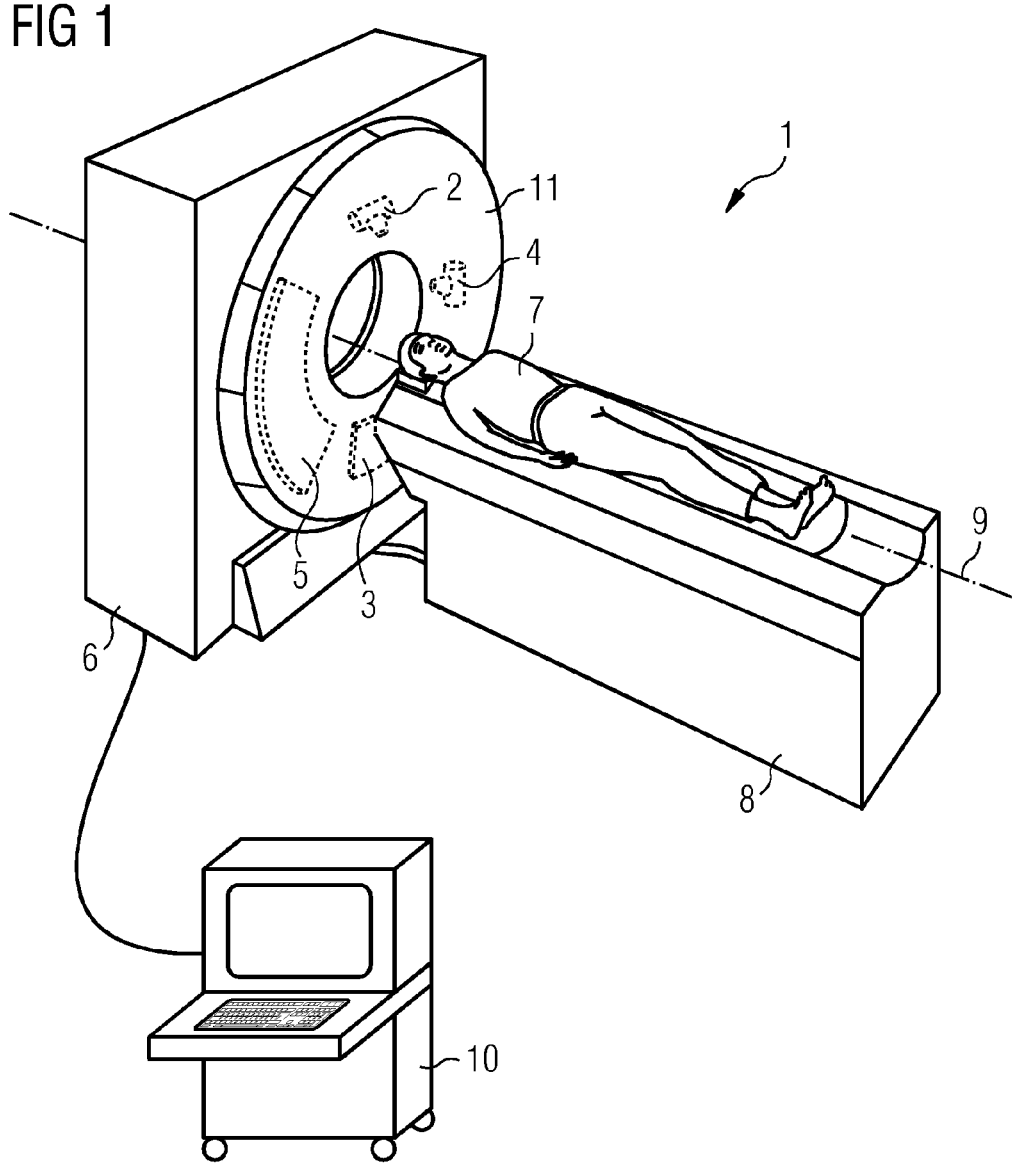
FIG. 1 shows an example of a computed tomography system.

FIG. 1 shows a computed tomography system 1 in accordance with the present teachings. The computed tomography system 1 includes a fixed gantry part 6. A rotatable gantry part 11 is located in the fixed gantry part 6. A first tube/detector system that includes an X-ray tube 2 and a detector 3 is arranged on the rotatable gantry part 11. Alternatively, one or more additional tube/detector systems may be fitted, as shown for example by the optional X-ray tube 4 and the optional detector 5 opposite thereto. To perform an examination, a patient 7 is brought into a measuring area using a patient couch 8 that is movable along a system axis 9. Absorption of the X-ray radiation from different projection angles may be measured. A computer 10 (e.g., a control and computation unit) is used for controlling the system 1. Computer programs that implement control of the system 1, evaluation of measured data, and reconstruction of desired tomographic image data run on the computer 10.

During transmission of detector data from the at least one detector 3 on the rotatable gantry part 11, a large quantity of accumulating data may be transmitted to the fixed gantry part 6. In addition, electrical power (e.g., for the power supply to the X-ray tube) may be transmitted from the fixed gantry part 6 to the rotatable gantry part 11. An apparatus in accordance with the present teachings for wireless transmission of electrical data signals and electrical power may be fitted on the rotatable gantry part 11 and the fixed gantry part 6. The signals and the power may be transmitted between the fixed gantry part 6 and the rotatable gantry part 11. The fixed gantry part 6 and the rotatable gantry part 11 are rotatable relative to one another. Exemplary embodiments of a configuration in accordance with the present teachings are described below in more detail in references to FIGS. 2 and 3.

Figure 2:
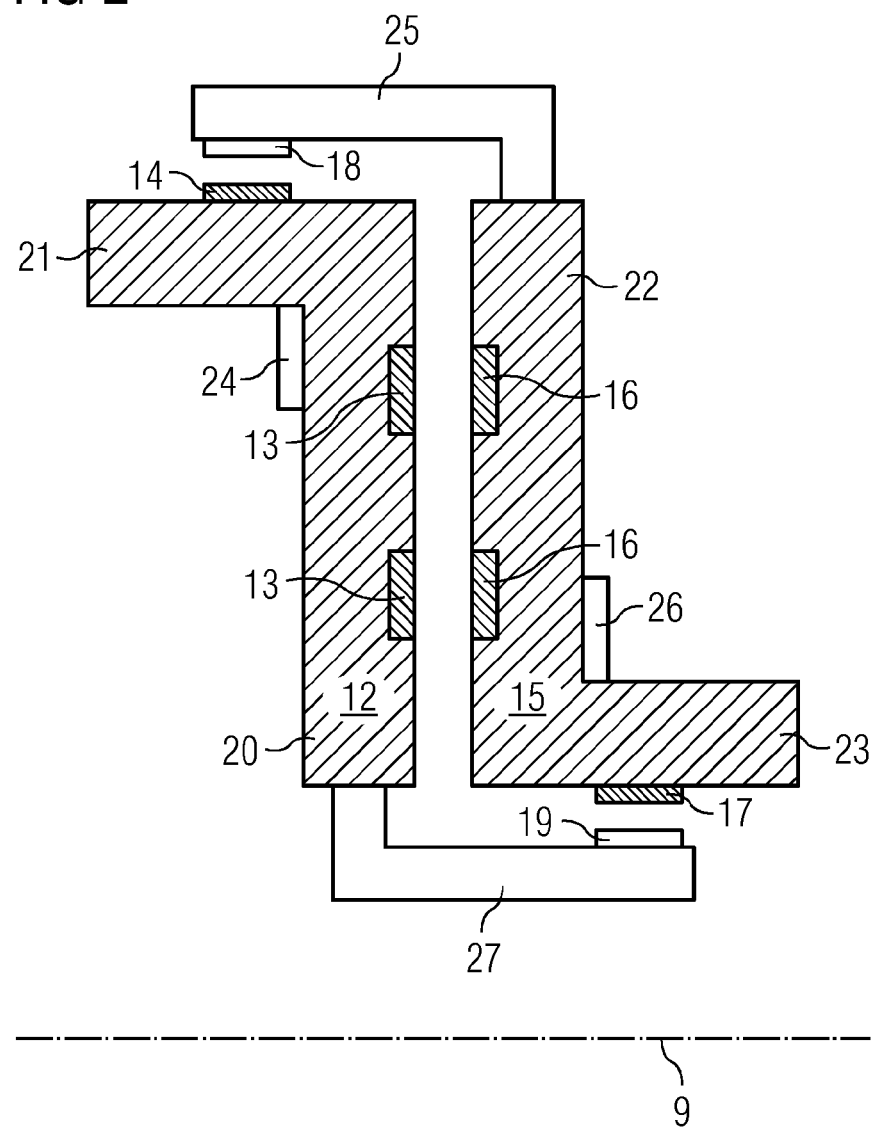
FIG. 2 shows a cross-sectional view through an exemplary first support ring and an exemplary second support ring with two data transmission paths.

FIG. 2 shows a cross-sectional view through a first support ring 12 and a second support ring 15 that are spaced apart from one another. The first support ring 12 and the second support ring 15 are rotatable with respect to one another. The first support ring 12 is mounted on a rotatable gantry part (not shown) of a computed tomography system. The second support ring 15 is arranged on the fixed gantry part (not shown). For simplicity, only the upper half of the cross-section through the axis of rotation 9 is shown in FIG. 2.

The cross-section of the first support ring 12 is in the form of an "L." The L-shape includes a long first limb 20 and a short first limb 21. The long first limb 20 and the short first limb 21 are at right angles to one another. The short first limb 21 is points away from the second support ring 15. Two first conductor elements 13 with a circular ring formation are arranged concentrically around the axis of rotation 9. The two first conductor elements 13 are provided on the outer side of the long first limb 20 (e.g., on the side facing the second support ring 15) and receive the electrical energy emitted by the second support ring 15. This electrical energy is passed on in order to supply power to components of the rotatable gantry part.

A second peripheral conductor element 14 is arranged concentrically around the axis of rotation 9. The second peripheral conductor element 14 is located on the outer side of the short first limb 21. Electrical first data signals generated by a first transmission module 24 may be emitted by the second conductor element 14. The first transmission module 24 rests on the inner side of the long first limb 20.

A second reception module 27 that includes a sixth conductor element 19 is arranged on the end of the long first limb 20. The sixth conductor element 19 is configured to receive electrical second data signals emitted by the second support ring 15.

The second support ring 15 is L-shaped in cross-section, and is arranged so as to have point symmetry with respect to the first support ring 12. The short second limb 23 of the second support ring 15 points away from the first support ring 12. The short second limb 23 is formed opposite the end of the long first limb 20.

Two third conductor elements 16 with a circular ring formation are arranged concentrically around the axis of rotation 9. The two third conductor elements 16 are provided in the outer side of the long second limb 22 (e.g., on the side facing the first support ring 12) and are configured to emit electrical energy for supplying power to components of the rotatable gantry part.

A fourth peripheral conductor element 17 is arranged concentrically around the axis of rotation 9. The fourth peripheral conductor element 17 is located on the outer side of the short second limb 23. Electrical second data signals generated by a second transmission module 26 may be emitted by the fourth conductor element 17. The second transmission module 26 rests on the inner side of the long second limb 22.

A first reception module 25 that includes a fifth conductor element 18 is arranged on the end of the long second limb 22. The fifth conductor element 18 is configured to receive the electrical first data signals emitted by the first support ring 12.

Figure 3:
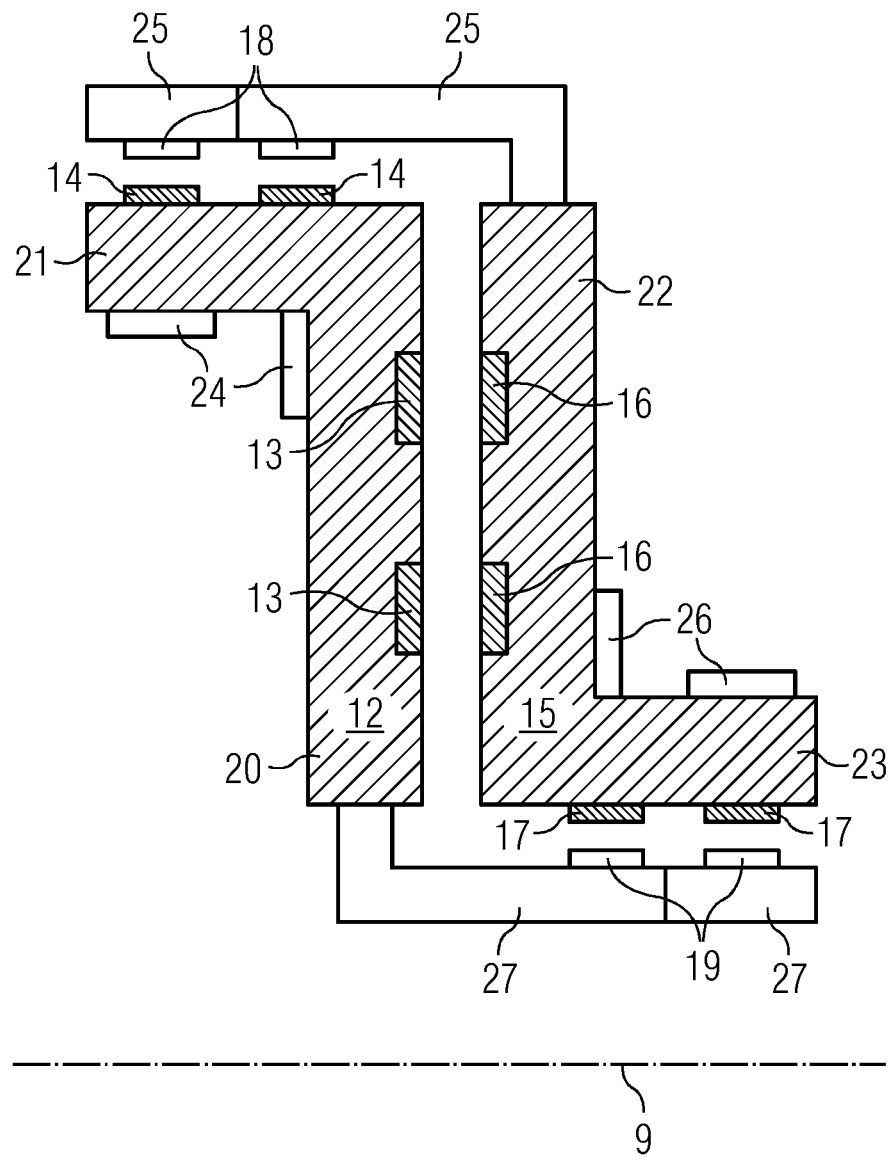
FIG. 3 shows a cross-sectional view through an exemplary first support ring and an exemplary second support ring with four data transmission paths.

FIG. 3 shows a configuration that is analogous to that shown in FIG. 2 except that the short first limb 21 and the short second limb 23 are provided with two second conductor elements 14 arranged in parallel or two fourth conductor elements 17 arranged in parallel. As shown in FIG. 3, two first reception modules 25 and two fifth conductor elements 18 or two second reception modules 27 and two sixth conductor elements 19 are provided. Two first transmission modules 24 and two second transmission modules 26 are also provided.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. An apparatus configured for wireless transmission of data and electrical power between a fixed gantry part and a rotatable gantry part, the rotatable gantry part configured to rotate about an axis of rotation of a computed tomography system, the apparatus comprising:
   a first support ring arranged on the rotatable gantry part; and
   a second support ring arranged on the fixed gantry part;
   wherein the first support ring and the second support ring are rotationally symmetrical and L-shaped in cross-section;
   wherein the first support ring comprises a short first limb and a long first limb;
   wherein the second support ring comprises a short second limb and a long second limb; and
   wherein the first support ring and the second support ring are configured to move relative to one another, such that the short first limb and the short second limb point away from one another and are not opposite one another.

2. The apparatus of claim 1, wherein the first support ring and the second support ring have point symmetry with respect to one another.

3. The apparatus of claim 2, further comprising:
   at least one conductor element arranged in or on an outer side of the long second limb and configured to output the electrical power; and
   at least one conductor element arranged in or on an outer side of the short second limb and configured to output electrical data signals.

4. The apparatus of claim 3, wherein each of the at least one conductor element arranged in or on the outer side of the long second limb and the at least one conductor element arranged in or on the outer side of the short second limb comprises a circular ring formation.

5. The apparatus of claim 1, further comprising:
   at least one first conductor element arranged in or on an outer side of the long first limb and configured to receive the electrical power; and
   at least one second conductor element arranged in or on an outer side of the short first limb and configured to transmit first electrical data signals.

6. The apparatus of claim 5, further comprising:
   at least one third conductor element arranged in or on an outer side of the long second limb and configured to output the electrical power; and
   at least one fourth conductor element arranged in or on an outer side of the short second limb and configured to output second electrical data signals.

7. The apparatus of claim 6, further comprising:
   at least one fifth conductor element arranged on the second support ring and configured to receive the first electrical data signals.

8. The apparatus of claim 7, further comprising:
   at least one sixth conductor element arranged in or on the first support ring and configured to receive the second electrical data signals.

9. The apparatus of claim 8, further comprising:
   a reception module arranged on the first support ring and configured to couple the second electrical data signals out of the sixth conductor element.

10. The apparatus of claim 7, further comprising:
    a first reception module arranged on the second support ring and configured to couple the first electrical data signals out of the fifth conductor element.

11. The apparatus of claim 7, further comprising:
    a transmission module arranged on the first support ring and configured to feed the first electrical data signals into the second conductor element.

12. The apparatus of claim 6, wherein each of the third conductor element and the fourth conductor element comprises a circular ring formation.

13. The apparatus of claim 6, further comprising:
    a transmission module arranged on the second support ring and configured to feed the second electrical data signals into the fourth conductor element.

14. The apparatus of claim 6, further comprising:
    at least one conductor element arranged in or on the first support ring and configured to receive the second electrical data signals.

15. The apparatus of claim 14, wherein each of the third conductor element and the fourth conductor element comprises a circular ring formation.

16. The apparatus of claim 6, further comprising:
    a transmission module arranged on the first support ring and configured to feed the first electrical data signals into the second conductor element.

17. The apparatus of claim 5, wherein each of the first conductor element and the second conductor element comprises a circular ring formation.

18. The apparatus of claim 5, further comprising:
    a first transmission module arranged on the first support ring and configured to feed the first electrical data signals into the second conductor element.

19. The apparatus of claim 5, further comprising:
    at least one conductor element arranged on the second support ring and configured to receive the first electrical data signals.

20. A computed tomography system comprising an apparatus configured for wireless transmission of data and electrical power between a fixed gantry part and a rotatable gantry part, the rotatable gantry part configured to rotate about an axis of rotation of the computed tomography system, the apparatus comprising:
    a first support ring arranged on the rotatable gantry part; and
    a second support ring arranged on the fixed gantry part;
    wherein the first support ring and the second support ring are rotationally symmetrical and L-shaped in cross-section;
    wherein the first support ring comprises a short first limb and a long first limb;
    wherein the second support ring comprises a short second limb and a long second limb; and
    wherein the first support ring and the second support ring are configured to move relative to one another, such that the short first limb and the short second limb point away from one another and are not opposite one another.

* * * * *